United States Patent [19]

Nakajima et al.

[11] Patent Number: 5,094,947

[45] Date of Patent: Mar. 10, 1992

[54] PROCESS FOR PRODUCING FRUCTOSE-1,6-DIPHOSPHATE

[75] Inventors: Hiroshi Nakajima; Masaaki Onda; Ryoichi Turutani; Hayato Ishihara, all of Kyoto, Japan

[73] Assignee: Unitika, Ltd., Hyogo, Japan

[21] Appl. No.: 758,481

[22] Filed: Sep. 9, 1991

Related U.S. Application Data

[63] Continuation of Ser. No. 486,695, Mar. 1, 1990, abandoned.

[30] Foreign Application Priority Data

Mar. 3, 1989 [JP] Japan .................................. 1-52616

[51] Int. Cl.$^5$ .......................... C12P 19/02; C12P 1/00
[52] U.S. Cl. ...................................... 435/105; 435/89; 435/92; 435/194; 435/94; 435/41; 435/219; 435/221; 435/252.5; 536/27; 536/28; 536/117
[58] Field of Search ............... 435/105, 89, 92, 194, 435/94, 41, 219, 221, 252.5; 536/27, 28, 117

[56] References Cited

U.S. PATENT DOCUMENTS

4,882,276  11/1989  Imahori et al. ...................... 435/89

FOREIGN PATENT DOCUMENTS

0202094  11/1986  European Pat. Off. ............... 435/41
2051078   1/1981  United Kingdom ............. 435/252.5

OTHER PUBLICATIONS

"Biochemistry", by A. L. Lehninger, 1970, pp. 319, 320 and 409.
"The Monosaccharides", Staněk et al., Academic Press, 1963, pp. 818-819.

*Primary Examiner*—Johnnie R. Brown
*Assistant Examiner*—Pamela S. Webber
*Attorney, Agent, or Firm*—Sughrue, Mion, Zinn, Macpeak & Seas

[57] ABSTRACT

A process for producing fructose-1,6-diphosphate comprising the steps of: (a) enzymatically converting adenosine 5'-diphosphate to adenosine 5'-triphosphate using an acetate kinase-containing microorganism or an extract of the microorganism and phosphate donor; and (b) enzymatically converting a substrate capable of being converted to glucose or fructose to fructose-1,6-diphosphate using the adenosine 5'-triphosphate resulting from step (a) and the acetate kinase-containing microorganism or the extract of the microorganism.

11 Claims, No Drawings

PROCESS FOR PRODUCING FRUCTOSE-1,6-DIPHOSPHATE

This is a continuation of application No. 07/486,695 filed Mar. 1, 1990, now abandoned.

FIELD OF THE INVENTION

The present invention relates to an enzymatic process for producing fructose-1,6-diphosphate.

BACKGROUND OF THE INVENTION

Fructose-1,6-diphosphate (hereinafter FDP) is a metabolic intermediate in the glycolytic pathway that is of graining importance in the field of medicines (Magalini S. I., Bondoli A., Scrascia E., *Resuscitation,* 5, 103 (1977) and Markov A. K., Oglethorpe N. C., Blake T. M., Lehan P. H., Hellems H. K., *Am. Heart J.,* 100, 639 (1980)). To meet this increase need for fructose-1,6-diphosphate, an industrial process for its production is desired.

At present, FDP is produced commercially using yeast mediated phosphorylation. This process uses yeast and a nutrient mixture containing glucose and inorganic phosphoric acid. The yeast to increase the permeability of its cell wall has been pre-treated with toluene, for example, is able to synthesize FDP through Harden-Young type fermentation (Seizaburo YAMAGUCHI, *Fermentation,* ed by Iwanami Zensho, 134–143 (1953)).

In JP-A-62-272977 (corresponding to German Patent Publication No. 3,709,718) (the term "JP-A" as used herein means an unexamined published Japanese patent application), this process has been improved by using enzymes that are effectively immobilized in the yeast by a glutaraldehyde treatment that prevents the enzymes from permeating out through the yeast cell wall. In addition, JP-A-63-87993 (corresponding to German Patent Publication No. 3,726,182 and British Patent Publication No. 2,196,967) teaches using hollow-fiber ultrafiltration to separate permeable substances from the yeast to allow continuous production of fructose-1,6-diphosphate. These are the only methods for the production of FDP used commercially at the moment.

A method as yet undeveloped to produce FDP in which a FDP synthesizing enzyme is reacted with a substrate in vitro is also possible. In this process, for example, using glucose as a substrate, FDP could be synthesized through the three step reaction shown below:

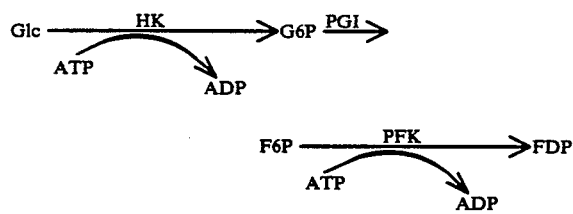

where the meaning of the symbols are as follows:
Glc: glucose, G6P: glucose-6-phosphate, F6P: fructose-6-phosphate,
FDP: fructose-1,6-diphosphate,
HX: hexokinase, PGI: phosphoglucose isomerase,
PFK: phosphofructokinase, ATP: adenosine-5'-triphosphate,
ADP: adenosine-5'-diphosphate.

In the above reaction, ATP must be continuously supplied to produce FDP because the ATP is consumed in both the first step and the third step of the reaction. This need for ATP, which is relatively expensive, prevents the use of this process for the commercial production of FDP.

Recently, an enzyme system has been developed which regenerates ATP in vitro from AMP (adenosine-5'-monophosphate) or ADP. Such an ATP-regeneration system is expected to allow ATP to be recycled, thus reducing its cost. This would enable industrial production of various useful substances using ATP. For example, by employing an adenylate kinase and an acetate kinase to convert AMP to ATP, with acetyl phosphate as a phosphate donor, a synthetic reaction system can be designed to produce physiologically active substances such as acetyl CoA, asparagine, pantothenic acid, and guanylic acid. See, JP-A-59-106296 (corresponding to Canadian Patent No. 1,194,825 and EP-A-84975). JP-A-54-122793 teaches a method in which ATP is supplied from an ATP-regeneration system employing acetate kinase, to produce glutathione from glutamic acid, cysteine, and glycine under the action of γ-glutamylcysteine synthetase.

The above-described methods utilizing the phosphorylating ability of yeast are necessarily accompanied by alcohol fermentation and the generation of ethanol and carbon dioxide in large quantities as by-products. As a result, the amount of FDP actually produced from the conversion of glucose is low. In addition, the separation of FDP from ethanol and carbon dioxide is extremely troublesome. Carbon dioxide is also a serious problem where a column reactor packed with yeast is employed. Yet another difficulty is the necessity, and expense of adding ATP or AND (nicotinamide adenine dinucleotide) as energy sources for the fermentation reaction It appears that a solution to the above problems would be an effective enzymatic process coupled with an ATP-regenerating system that does not give ethanol and carbon dioxide as by-products, and achieves a high conversion efficiency. Such a system would require the use of purified enzymes for the ATP-regeneration system and the physiologically-active-substance-synthesizing system. The purification of such enzymes takes considerable time and involves significant labor despite recent progress in the separation and purification of natural high-molecular substances such as enzymes. Accordingly, such enzymatic processes have not been economically feasible.

As mentioned above, current methods for producing fructose-1,6-diphosphate all involve such problems as the generation of unwanted by-products, a low conversion efficiency, and the necessity of extensive enzyme purification.

SUMMARY OF THE INVENTION

An object of the present invention is to provide a process for producing fructose-1,6-diphosphate, which is advantageous industrially because there is no formation of by-products, it has a high conversion rate, and no extensive enzyme purification is required.

As the result of substantial investigation to solve these problems, the inventors have found that in the described enzymatic synthesis, fructose-1,6-diphosphate is formed and is accumulated in an unexpected amount by coupling an ATP-regeneration system with the synthesis system of fructose-1,6-diphosphate, and by using an acetate kinase-containing microorganism or extract thereof as the catalyst for both reaction systems.

The present invention provides a process for producing fructose-1,6-diphosphate comprising the steps of:
  a process for producing fructose 1,6-diphosphate comprising steps of:
    (a) enzymatically converting adenosine 5'-diphosphate to adenosine 5'-triphosphate using an acetate kinase-containing microorganism or an extract of the microorganism and phosphate donor; and
    (b) enzymatically converting a substrate capable of being converted to glucose or fructose to fructose 1,6-diphosphate using the adenosine 5'-triphosphate resulting from step (a) and the acetate kinase-containing microorganism or the extract of the microorganism.

The present invention allows advantageous production of fructose-1,6-diphosphate with remarkably high efficiency without the formation of ethanol and carbon dioxide and without the necessity of purifying enzyme catalysts. Accordingly, the present invention provides an industrially advantageous process for producing fructose-1,6-diphosphate useful extensively for medicines.

DETAILED DESCRIPTION OF THE INVENTION

The process for producing fructose-1,6-diphosphate of the present invention constitutes an ATP-regeneration system to form ATP from ADP, and an FDP synthesis system to synthesize fructose-1,6-diphosphate from a substrate. These reaction systems are coupled and both are catalyzed by an acetate kinase-containing microorganism or extract thereof.

The ATP-regeneration system of the present invention is known to be catalyzed by acetate kinase (E.C.2.7.2.1) as described, for example, in H. Nakajima et al, *J. Biochem.*, 84, 193-203 (1978). In the present invention, an acetate kinase-containing microorganism or extract of a microorganism is used as the source of acetate kinase for the ATP-regeneration reaction system and acetyl phosphate, propionyl phosphate or methoxycarbonyl phosphate is used as the phosphate donor.

The fructose-1,6-diphosphate-synthesizing system of the present invention is known to be catalyzed by glycolysis enzymes such as hexokinase, glucokinase, phosphoglucoseisomerase, or phosphofructokinase (all of which use glucose as a substrate). The inventors of the present invention have surprisingly found, in addition to a mixture of these enzymes, that the FDP synthesis system is additionally catalyzed by a microorganism or extract of a microorganism containing acetate kinase. The ATP, consumed in the FDP synthesis system by the hexokinase or glucokinase, and phosphofructokinase in the FDP synthesis system, is supplied from the above-described ATP-regeneration system.

Any microorganism or its extract containing acetate kinase may be used without restriction in the present invention. The followings are representative examples of genera that include microorganisms containing acetate kinase. Lactobacillus; Escherichia (such as *E. coli*); Proteus; Streptococcus: Veillonea; Desulfovibrio; Propionibacterium; Bacillus (such as *B. stearothermophilus, B. brevis, B. coaqulus, B. thermoproteolyticus, and B. acidocardarius*); Clostridium: Thermoactinomyces; Achromobacter: Streptomyces; Micropolyspora: Thermoas (such as *T. acuaticus, thermophilus*, and *T. flavus*); Thermomicrobius; Carderia. In addition, microorganisms into which a gene for acetate kinase has been introduced may also be used.

The content of acetate kinase in the microorganisms is not particularly limited, but is preferably 5,000 units or higher, more preferably 10,000 units or higher, still more preferably 50,000 or higher per kg of wet microorganism.

preferred microorganism according to the present invention is *Bacillus stearothermophilus* (e.g., NCA-1503 strain (ATCC 29609) or the like. This *Bacillus stearothermophilus* strain is a thermophilic bacteria that has a high acetate kinase content.

Measurement of acetate kinase activity

"Acetate kinase content" as used throughout this application was determined using the following technique.

To 1 g of wet microorganisms obtained from a liquid culture medium by centrifugation (5,000 rpm for 15 min. at 4° C.), 4 ml of 25 mM potassium phosphate buffer solution (pH: 7.5,) was added to prepare a suspension. The microorganisms were crushed by ultrasonic crushing for 10 minutes using a sonic oscillator (made by Kubota Seisakusho K. K.) at 1.5 A, and again centrifuged (5,000 rpm for 15 min. at 4° C.) to prepare a sample of crushed microorganism-containing liquid.

Subsequently, a 50 mM imidazole-hydrochloric acid buffer solution (pH: 7.2) was prepared which contained 10 mM of ATP, 3.4 mM of phosphoenolpyruvic acid, 0.26 mM of NADH, 20 mM of $MgCl_2$, 75 mM of KCl, and 400 mM of sodium acetate. Per 1 ml of this solution, was added 2 $\mu$l of lactate dehydrogenase (10 mg/ml in glycerin swine-muscle-origin, made by Behlinger Mannheim Co.), and 2 $\mu$l of pyruvate kinase (suspension in ammonium sulfate solution swine-heart-origin, made by Oriental Yeast Co., Ltd.). This mixture was preliminarily heated to 30° C., and a 1 to 50 $\mu$l of the test sample was added thereto to start the reaction. The rate of decrease of NADH was measured by the decrease of 340 nm light absorbed. The rate of phosphorylation of the acetic acid was calculated from this absorbance. One unit of acetate kinase activity is defined as the quantity of enzyme required to phosphorylate the sodium acetate at a rate of 1 $\mu$mol per minute under the conditions described above.

The microorganism or its extract for use in the present invention may be obtained by culturing any appropriate microorganism using known culture mediums suitable for the chosen organism. For example, *Bacillus stearothermophilus* NCA-1503 strain (ATCC 29609) may be cultured using the medium and conditions described below.

The carbon source for the culture medium is preferably glucose or sucrose at a concentration preferably from 0.1 to 1.0%, more preferably from 0.3 to 0.5%. The nitrogen source may be peptone, casamino acid, cultivator (fish meat extract) at a concentration, preferably from 0.05 to 0.5% for peptone. The vitamin source may be yeast extract, corn steep liquor, or meat extract at a concentration, preferably from 0.1 to 0.5% for yeast extract. The culture medium may additionally contain sulfur, phosphorus, and/or other essential minerals in any available from such as in an inorganic salt. Cultivation of the chosen microorganism may be, for example, at pH 5 to 8 and at a temperature of 55° to 60° C. using aeration-agitation.

The microorganisms may be recovered from the culture medium by any known method such as centrifugation.

The microorganisms used in the present invention include untreated living microorganisms as separated from a culture medium, dried or freeze-dried microorganisms, microorganisms treated with organic solvent or surfactant, and microorganisms treated by temperature shock or osmotic shock. These treatments may be according to any known method. In order to raise the efficiency of the described reaction, it is preferable to conduct treatments that increase permeability of phosphate donor and fructose-1,6-diphosphate through the cell wall of the chosen microorganism.

The extract of the microorganisms may be prepared by bacteriolysis such as by autolysis; by treatment with bacteriophage; by treatment with a chemical like an organic solvent or a surfactant; by enzyme treatment; by mechanical force; by thermal shock; by osmotic shock; or according to known methods.

If the FDP synthesis system needs another enzyme in addition to the enzyme contained in the above-mentioned microorganisms, there may properly be added, to the production system of the present invention, a commercial product of the needed enzyme, or microorganisms or an extract thereof containing the needed enzyme obtained as mentioned above. In such a case also, the enzyme need not be purified at all.

For example, when lactose is used as the substrate, commercial β-galactosidase (made by Sigma Co., for example of *Asperqillus oryzae*-origin or *Escherichia coli*-origin) may be used together with *Bacillus stearothermophilus* or its extract containing the acetate kinase. Alternatively, β-galactosidase-containing microorganisms such as *Aspergillus oryzae* cultured in a lactose-containing medium or the extract of the body of β-galactosidase-containing microorganisms may be used together with acetate kinase-containing *Bacillus stearothermophilus* or extract thereof.

The production of FDP in the present invention may be practiced by reacting together a substrate for the synthesis of FDP, phosphate doner in the ATP-regeneration system, and the above-mentioned microorganism or its extract. Specifically, for example, the microorganism or its extract is added to and blended into a solution containing a substrate, other enzymes and phosphate donor.

The choice of substrate is not limited in any way so long as it is capable of ultimately being converted to fructose-1,6-diphosphate. There may be used, for example, monosaccharides such as glucose or fructose; disaccharides such as lactose or sucrose; or polysaccharides such as starch. Although the substrate concentration may be 1M or higher in the solution, it is preferably in the range of from 10 mM to 1M when glucose is used as the substrate.

A magnesium salt, an ammonium salt, ATP, a buffer solution, and/or other additives known in the art may be contained in the solution in addition to the substrate. Any salt of magnesium or ammonium may be used so long as it does not inhibit the enzyme reactions. Some useful magnesium salts are, for example, magnesium chloride, magnesium acetate and magnesium sulfate. Useful ammonium salts, are, for example, ammonium sulfate, ammonium acetate, and ammonium chloride. Aqueous ammonia may also be used. The concentration of the salt is preferably in the range of from 0.1 to 100 mM.

The concentration of the ATP may be 2 mM or higher, but preferably is kept in the range of from 0.1 to 2 mM because of its cost.

Any buffer solution may be used which has a buffering capacity in the pH range of about from 4 to 10, preferably in the pH range of about from 5 to 9. Examples of buffer solution that can be used are those formulated with acetate, tris, imidazole, phosphate, and borate. The concentration of the buffer solution used is preferably in the range of from about 1 to 1000 mM, more preferably from about 2 to 100 mM.

The ratio of the microorganism or its extract to be added to the solution depends on the content of acetate kinase in the microorganism, and is preferably not less than 1 unit of acetate kinase activity per 1 liter of solution, more preferably not less than 100 units of acetate kinase activity per 1 liter of solution. Although it is difficult to give a precise value, normally not less than 0.01 g, more preferably 0.1 to 10 g of wet microorganism per 1 liter of the mixed solution is necessary.

The phosphate donor employed in the present invention may either be in the form of a free acid or a neutralized salt. Preferably, it is in the form of neutral salt such as an ammonium salt, a lithium salt, a sodium salt, or a potassium salt.

An ordinary commercial product may be used as the phosphate donor. Alternatively, a synthesized product may be used which is prepared, for example, according to the method of J. M. Whiteside et al. (*The Journal of Orqanic Chemistry.* 44, 864 (1970)). The amount of phosphate donor to be added in the present invention is decided in consideration of the amount of acetate kinase coming from the microorganism or its extract, and is in the range of from 0.01 to 12 mM, preferably from 0.1 to 6 mM per hour for about 100 units of acetate kinase activity.

The pH value in the reaction of the present invention is maintained in the range of from 4 to 10, preferably from 5 to 9. The pH may be maintained within the value by addition of alkali or by a similar method. If alkali is used, any alkali, such as sodium hydroxide, may be used which does not inhibit the reaction.

The reaction temperature may be within the range of from 0° to 80° C., preferably from 20° to 60° C. If the microorganism or its extract is derived from a thermophilic microorganism, the reaction can proceed suitably above room temperature.

The process of the present invention may be carried out in a batch process, for example, by employing a reaction vessel. The process may also be carried out, in a continuous process, using a column type reactor which contains the microorganism or extract immobilized on a high molecular weight carrier or included in and crosslinked to a high molecular weight carrier packed in the column; or using a film type reactor which contains the microorganism or extract enclosed in a film.

The reaction time depends on the reaction conditions. In a batch process, the time of several hours to 24 hours is normally convenient in view of the operations involved. In a continuous process employing, for example, a column type reactor, the ratio of the volume of the solution flowing along the column per hour to the column volume is desirably maintained at one or less.

The fructose-1,6-diphosphate is separated from the resulting reaction solution and is purified. Known purification methods such as a precipitation method using a calcium salt or a barium salt *Arch. of Biochem,* 3, 33–44,(1943)); or a column separation method (JP-A-60-156697 (correponding to U.S. Pat. No. 4,575,549)); or the like may be employed.

The present invention is further described in the following non-limiting examples.

The fructose-1,6-diphosphate obtained from the examples was analyzed using an enzymatic method described in the literature: Bergmeyer, *Methods of Enzymatic Analysis*, 3rd Ed., 6, 342, Bahlag Chemie Co. The phosphate, sodium and chlorine ions were analyzed using ion chromatography. A Model L-6200 intelligent pump and Model L-3270 electroconductivity meter (HITACHI, LTD.) with a Column 2730(4 cm in diameter, 50 cm in length (Hitachi, Ltd.) with an aqueous solution of 0.7 mM-KOH and 0.03 mM-citric acid as a solvent at a flow rate of 1.0 ml/min were used to analyze for phosphate and chlorine ions, and a Column 2720 (4 cm in diameter, 50 cm in length (Hitachi, Ltd.)) was used with an aqueous solution of 0.8 mM nitric acid as a solvent at a flow rate of 1.0 ml/min were used to analyze for sodium ions. Water content was measured with a moisture meter, Model AQ-6 (Hiranuma Sangyo K. K.).

In the following description, "percent (%)" is based on total weight.

REFERENCE EXAMPLE

Acetyl phosphate was prepared by dissolving 400 ml of 85%-phosphoric acid (6 moles of phosphoric acid) in about 4 liters of ethyl acetate. To this was added 1.2 liters (12 mols) of acetic anhydride (the amount needed to yield a molar ratio of 2:1 for acetic anhydride to phosphoric acid). This operation was carried out with gentle stirring while maintaining the temperature at 5° C. for 30 minutes. Thereafter, the stirring was continued for 2 hours while keeping the temperature at 5° C. At the end of this time, 4.5 liters of water were added, and the mixture neutralized by adding 500 g of sodium bicarbonate. The aqueous layer containing sodium acetyl phosphate was removed. About 5 liters of aqueous sodium acetyl phosphate solution was obtained. To this aqueous acetyl phosphate solution was added an approximately equal amount of ethyl acetate. This combination was agitated, and the aqueous layer separated. This washing treatment with ethyl acetate was repeated several times. Ultimately, approximately 5 liters of an aqueous solution of containing approximately 900 mM sodium acetyl phosphate was obtained. This sodium acetyl phosphate solution was frozen for storage.

EXAMPLE 1

*Bacillus stearothermophilus* NCA-1503 strain (ATCC 29609) was inoculated into 500 liters of a culture medium containing 0.35% of glucose, 0.30% of yeast extract, 0.10% of peptone, 0.10% of $KH_2PO_4$, 0.10% of $Na_2HPO_4.12H_2O$, 0.05% of $MgSO_4.7H_2O$, 5 mg/l of ferrous sulfate, 5 mg/l of calcium hydroxide, 1 mg/l of manganese sulfate, and 1 mg/l of sodium molybdate. The pH of the culture medium was adjusted with 4N sodium hydroxide to the range of from 6.8 to 7.2 at a temperature of from 58° to 60° C. The cultivation method was repeated several times. The microorganisms were recovered from the culture medium by centrifugation, and stored frozen.

500 g of frozen microorganisms were suspended in 2 liters of a 25 mM-potassium phosphate buffer solution (pH: 7.6) containing 1M of glucose and 4 mM of EDTA. To this suspension was added 500 mg of egg-white lyzozyme. The mixture was maintained at a temperature of 30° C. After standing for 2 hours, the microorganisms were crushed, and the acetate kinase activity was determined to be 53,400 units per liter.

The above-described solution contained 500 g of crushed microorganisms. It was added to a 800-liter reaction vessel containing 300 liters of 10 mM thishydrochloric acid buffer solution at pH 7.6 containing 300 mM of glucose, 1 mM of ATP, 5 mM of ammonium sulfate, and 20 mM of $MgCl_2$ at 30° C. The temperature of the reaction vessel was maintained at 30° C. throughout the reaction. To this 300 liters of reaction solution, an aqueous solution of approximately 900 mM of sodium acetyl phosphate prepared as in the Reference Example, above, was added to start the synthesis of fructose-1,6-diphosphate. The acetyl phosphate was continuously added to the reaction solution in the reaction vessel at a rate of 5 liters per hour. The pH lowering that accompanied the addition of the acetyl phosphate was compensated for by the addition of a sufficient amount of 4N sodium hydroxide to maintain the pH at 7.6. The reaction was stopped after about 40 hours when 200 liters, total, of acetyl phosphate solution had been added.

The final volume of the solution was 500 liters and contained 171 mM of fructose-1,6-diphosphate, and 23 mM of phosphate. The yield of fructose-1,6-diphosphate from the glucose substrate was 93%.

The pH of the solution after the reaction was adjusted to pH 2 by the addition of hydrochloric acid. The resulting precipitate was eliminated by centrifugation. The clear supernatant was neutralized with sodium hydroxide; and an aqueous solution of 3 kg of calcium chloride in 20 liters of water was added. This mixture was stirred, and the resulting calcium phosphate eliminated by a Yabuta-type filter press to produce clear filtrate. An additional 10 kg of calcium chloride (solid) was added to this filtrate, and the resulting mixture maintained at 80° C. A precipitate formed, and was recovered by a filter press, washed with water, and dried by a vacuum drier, to yield 39.4 kg of dicalcium fructose-1,6-diphosphate as the product.

This product had a composition of 67.0% fructose-1,6-diphosphoric acid, 15.8% of calcium and 14.7% of moisture. The yield of the fructose-1,6-diphosphoric acid was 91.0%.

EXAMPLE 2

*Propionibacterium freudenreichii* IFO12425 was inoculated into 10 liters of a culture medium (pH: 6.5) containing 0.35% of glucose, 0.30% of peptone, 0.30% of yeast extract, and 0.05% of $KH_2PO_4$. This bacteria was cultured at 30° C. using a jar fermenter; 20 g of wet microorganisms were collected by centrifugation and immersed in acetone for 2 hours. Separately, 30 liters of tris-HCl solution prepared in the same manner as in Example 1 was placed in a 70-liter reaction vessel. To the tris-HCl solution was added 20 g of the acetone-treated microorganism body. The resulting solution was maintained at 30° C., and 20 liters of acetyl phosphate prepared as in the Reference Example was added in 5-liter portions. The reaction solution yielded 3.6 kg of dicalcium fructose-1,6-diphosphate salt following treatment with calcium chloride in the same manner as described in Example 1.

The product had a composition nearly the same as that of Example 1. The reaction yield from the glucose substrate was 91%, and the purification yield was 92%.

EXAMPLE 3

*Escherichia coli* C600 (supplied by Funakoshi Yakuhin K. K.) was cultured and 60 g of the resulting wet microorganisms freeze-dried. Kneaded into the freeze-dried microorganisms were 50 ml of aqueous 10% gelatin solution. The kneaded product was passed through a strainer, and permeated with a 5% glutaraldehyde solution. After washing, it was packed in a column of 2 cm in diameter and 25 cm in length. The packed column was maintained at a temperature of 30° C. Through this column, 10 mM tris-hydrochloric acid buffer solution containing 100 mM of glucose, 0.5 mM of ATP, 3 mM of ammonium sulfate, 10 mM of $MgCl_2$, and 200 mM of acetyl phosphate was made to flow at a rate of 60 ml per hour. Reacted solution was stored at 4° C. in an refrigerator. After continuous reaction in such a manner for 5 days, 6.6 liters of the reacted solution was obtained. This reacted solution contained 94 mM of fructose-1,6-diphosphoric acid, and 17 mM of phosphoric acid.

An anion-exchange resin column 5 cm in diameter and 50 cm in length (Dowex SAR, made by Muromachi Kagaku Kogyo K. K.) was brought to equilibrium using an aqueous solution containing 0.04M sodium chloride and 0.01N hydrochloric acid. The above-mentioned 6.6 liters of fructose-1,6-diphosphate solution was put on the column. The column was then washed with about 30 liters of the equilibrating solution. Thereafter, the fructose-1,6-diphosphate was eluted using 20 liters of an aqueous solution containing 0.4M sodium chloride and 0.01N hydrochloric acid, resulting in 20 liters of an aqueous 26 mM fructose-1,6-diphosphate solution free from phosphate. Sodium chloride was eliminated from this aqueous fructose-1,6-diphosphate solution by means of an electrodialysis apparatus (Model G-3, dialysis membrane AC-110-800 made by Asahi Kasei Kogyo K. K.). The dialyzed solution was concentrated by rotary evaporation and freeze-dried, to give 232 g of powdery sodium fructose-1,6-diphosphate.

This product had a composition of 73.3% of fructose-1,6-diphosphoric acid, 14.9% of sodium 0.5% of sodium chloride, 0.6% of phosphoric acid, and 10.5% of moisture. The purification yield was 81%.

EXAMPLE 4

Using 60 g of wet *B. stearothermophilus* cultured as in Example 1, a column was packed and reacted as described in Example 3, to give powdery sodium fructose-1,6-diphosphate. This product had a composition of 72.6% of fructose-1,6diphosphoric acid, 14.7% of sodium, 0.5% of sodium chloride, 0.4% of phosphoric acid, 12.0% of moisture. The purification yield was 85%.

While the invention has been described in detail and with reference to specific examples thereof, it will be apparent to one skilled in the art that various changes and modifications can be made therein without departing from the spirit and scope thereof.

What is claimed is:

1. A process for producing fructose-1,6-diphosphate consisting essentially of the steps of:
   (a) culturing a microorganism which contains the enzymes acetate kinase, at least one of hexokinase or glucokinase, phosphoglucose isomerase and phosphofructokinase;
   (b) reacting said cultured microorganism or an extract of said cultured microorganism containing said enzymes with glucose, adenosine 5'-triphosphate and a phosphate donor in a reactor comprising two coupled reactions where (i) adenosine 5'-triphosphate is enzymatically produced from adenosine 5'-diphosphate generated from reaction (ii) using said phosphate donor and said acetate kinase; and (ii) fructose-1,6-diphosphate is enzymatically synthesized from glucose using adenosine 5'triphosphate produced in reaction (i) by one of hexokinase or glucokinase, phosphoglucose isomerase and phosphofructokinase comprising three reactions; and
   (c) recovering the resulting fructose-1,6-diphosphate from said reaction solution of step (b).

2. A process for producing fructose-1,6-diphosphate consisting essentially of the steps of:
   (a) culturing a microorganism which contains the enzymes acetate kinase, hexokinase and phosphofructokinase;
   (b) reacting said cultured microorganism or an extract of said cultured microorganism containing said enzymes with fructose, adenosine 5'-triphosphate and a phosphate donor in a reactor comprising two coupled reactions wherein (i) adenosine 5'-triphosphate is enzymatically produced from adenosine 5'-diphosphate generated from reaction (ii) using said phosphate donor and said acetate kinase; and (ii) fructose-1,6-diphosphate is enzymatically synthesized from fructose using adenosine 5'triphosphate produced in reaction (i) by hexokinase and phosphofructokinase comprising two reactions; and
   (c) recovering the resulting fructose-1,6-diphosphate from said reaction solution of step (b).

3. The process for producing fructose-1,6-diphosphate of claim 1 or 2, wherein said extract of said cultured microorganism is obtained by treating said cultured microorganism chemically or physically.

4. The process for producing fructose-1,6-diphosphate of claim 1 or 2, wherein said steps (b) and (c) are conducted at the same time using a film type reactor.

5. The process for producing fructose-1,6-diphosphate of claim 1 or 2, wherein said phosphate donor is acetyl phosphate.

6. The process for producing fructose-1,6-diphosphate of claim 1 or 2, wherein the concentration of said glucose or fructose is from about 10 mM to about 1M.

7. The process for producing fructose-1,6-diphosphate of claim 1 or 2, wherein said microorganism to be cultured is a microorganism belonging to a genus selected from the group consisting of Lactobacillus, Escherichia, Proteus, Streptococcus, Veillonea, Desulfovibrio, Propionibacterium, Bacillus, Clostridium, Thermoactinomyces, Achromobacter, Streptomyces, Micropolyspora, Thermoas, Thermomicrobius and Carderia.

8. The process for producing fructose-1,6-diphosphate of claim 7, wherein said microorganism is *Bacillus stearothermophilus*, strain NCA-1503, ATCC 29609.

9. The process for producing fructose-1,6-diphosphate of claim 1 or 2, wherein said microorganism to be cultured contains at least 5,000 units of acetate kinase per kg wet weight of microorganism.

10. The process for producing fructose-1,6-diphosphate of claim 9, wherein said microorganism contains at least 10,000 units of acetate kinase per kg wet weight of microorganism.

11. The process for producing fructose-1,6-diphosphate of claim 9, wherein said microorganism contains at least 50,000 units of acetate kinase per kg wet weight of microorganism.

* * * * *